United States Patent

Sartorelli et al.

Patent Number: 5,281,715
Date of Patent: Jan. 25, 1994

[54] 2-FORMYLPYRIDINE THIOSEMICARBAZONE COMPOUNDS

[75] Inventors: Alan C. Sartorelli, Woodbridge; Tai-Shun Lin, North Haven, both of Conn.

[73] Assignee: Yale University, New Haven, Conn.

[21] Appl. No.: 882,154

[22] Filed: May 13, 1992

[51] Int. Cl.$^5$ .......................................... C07D 213/02
[52] U.S. Cl. .................................... 546/306; 546/331
[58] Field of Search ............... 546/308, 309, 336, 306, 546/331

[56] References Cited

PUBLICATIONS

Chemical Abstracts, vol. 104, No. 5, Abstract 28370k, p. 13, Feb. 3, 1986.

K. C. Agrawal et al., "Potential Antitumor Agents. 13. 4-Methyl-5-Amino-1-Formylisoquinoline Thiosemicarbazone," J. Med. Chem., vol. 19, pp. 970-972 (1976).

K. C. Agrawal et al., "4-Methyl-5-Amino-1-Formylisoquinoline Thiosemicarbazone, a Second-Generation Antineoplastic Agent of the α-(N)-Heterocyclic Carboxaldehyde Thiosemicarbazone Series," Cancer Res., vol. 37, pp. 1692-1696 (1977).

F. A. French et al., "α-(N)-Formylheteroaromatic Thiosemicarbazones. Inhibition of Tumor-Derived Ribonucleoside Diphosphate Reductase and Correlation with In Vivo Antitumor Activity," J. Med. Chem., vol. 17, pp. 172-181 (1974).

L. Achremowicz et al., "Reactions of 3-Nitropicolines N-Oxides with Acetic Anhydride," Roczniki Chemii, vol. 46, pp. 409-419 (1972).

M. C. Liu et al., "A One-Pot Synthesis of 3-Nitro- and 3,5-Dinitro-2-Picolines," Synth. Commun., vol. 20(19), pp. 2965-2970 (1990).

E. J. Blanz, Jr. et al., "The Carcinostatic Activity of 5-Hydroxy-2-Formylpyridine Thiosemicarbazone," Cancer Res., vol. 28, pp. 2419-2422 (1968).

K. C. Agrawal et al., "Potential Antitumor Agents. 9.2-Formyl(m-Amino)Phenylpyridine Thiosemicarbazones," J. Med. Chem., vol. 17, No. 6, pp. 631-635 (1974).

K. C. Agrawal et al., "Potential Antitumor Agents. 14. 4-Substituted 2-Formylpyridine Thiosemicarbazones," J. Med. Chem., vol. 19, No. 10, pp. 1209-1214 (1976).

S. Furukawa, "Synthesis of Pyridine Derivatives. VII. Nitration of 2,4-Lutidine," J. Pharm. Soc. Japan, vol. 76, pp. 900-902 (1956).

R. H. Dodd et al., "Hybrid Molecules: Growth Inhibition of Leishmania donovani Promastigotes by Thiosemicarbazones of 3-Carboxy-β-Carbolines," J. Med. Chem., vol. 32, No. 6, pp. 1272-1276 (1989).

(List continued on next page.)

Primary Examiner—C. Warren Ivy
Assistant Examiner—Zinna N. Davis
Attorney, Agent, or Firm—Wegner, Cantor, Mueller & Player

[57] ABSTRACT

A method of treatment of tumors is provided based upon a compound of the formula

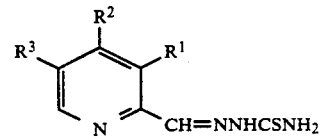

wherein
one of $R^1$ is $NHR^4$ or $NR^4R^5$ or $R^3$ is $NHR^4$, $NR^4R^5$ or OH, and the other is hydrogen;
$R^2$ is hydrogen or $C_{1-4}$ lower alkyl;
$R^4$ is hydrogen, hydroxyl or $C_{1-4}$ lower alkyl; and
$R^5$ is $C_{1-4}$ lower alkyl;

or a pharmaceutically acceptable salt or hydrate thereof.

In a further aspect there is provided a method for the treatment of a tumor in a mammal which comprises administration of a compound which is 3- or 5-hydroxy-4-methyl-2-formylpyridine thiosemicarbazone to said mammal.

7 Claims, No Drawings

PUBLICATIONS

E. J. Corey et al., "Studies on the Mechanism of Oxidation of Ketones by Selenium Dioxide (Part I)," J. Am. Chem. Soc., vol. 82, pp. 918–929 (1960).

T. S. Lin et al., "Synthesis of 2,3-Diaziridinyl-1,4-Naphthoquinone Sulfonate Derivatives as Potential Antineoplastic Agents," J. Med. Chem., vol. 32, No. 7, pp. 1467–1471 (1989).

A. C. Sartorelli et al., "Mechanism of Inhibition of Ribonucleoside Diphosphate Reductase by α-(N-)-Heterocyclic Aldehyde Thiosemicarbazones," Biochem. Pharmacol., vol. 20, pp. 3119–3123 (1971).

H. L. Elford et al., "Ribonucleotide Reductase and Cell Proliferation I. Variations of Ribonucleotide Reductase Activity with Tumor Growth Rate in a Series of Rat Hepatomas," J. Biol. Chem., vol. 245, pp. 5228–5233 (1970).

R. C. DeConti et al., "Clinical and Pharmacological Studies with 5-Hydroxy-2-Formylpyridine Thiosemicarbazone," Cancer Res., vol. 32, pp. 1455–1462 (1972).

I. H. Krakoff et al., "Clinical Trial of 5-Hydroxypicolinaldehyde Thiosemicarbazone (5-HP; NSC-107392), With Special Reference to Its Iron-Chelating Properties," Cancer Chemother. Rep., vol. 58, pp. 207–212 (1974).

E. C. Moore et al., "Inhibition of Deoxyribonucleotide Synthesis by Pyridine Carboxaldehyde Thiosemicarbazones," Cancer Res., vol. 31, pp. 235–238 (1971).

2-FORMYLPYRIDINE THIOSEMICARBAZONE COMPOUNDS

RESEARCH GRANT

Some aspects of the invention were supported in part by U.S. Public Health Service Grant CA-02817 from the National Cancer Institute and support from the Northeast NMR Facility at Yale University insofar as the use of high resolution NMR spectra is concerned that was made possible by a grant from the Chemical Division of the National Science Foundation (Grant No. CHE-7916210).

INFORMATION DISCLOSURE UNDER 37 CFR § 1.97

5-Hydroxy-2-formylpyridine thiosemicarbazone is a well known compound that has been proposed as an anti-neoplastic agent and has received a Phase I trial in cancer patients. This agent was not chose for further development. Representative literature includes DeConti et al., "Clinical and Pharmacological Studies with 5-Hydroxy-2-formylpyridine Thiosemicarbazone", *Cancer Res.*, 1972, 32, 1455-62. Similarly, 4-methyl-5-amino-1-formylisoquinoline thiosemicarbazone is also well known as manifested by Agrawal et al., "Potential Antitumor Agents. 13. 4-Methyl-5-amino-1-formylisoquinoline thiosemicarbazone", *J. Med. Chem.*, 1976, 19, 970-72. Subsequent to this research, others have tried a variety of compounds which may be considered to be analogs of 2-formylpyridine thiosemicarbazones, as shown by the numerous compounds which have been synthesized and tested by French et al., "α-(N)-Formylheteroaromatic Thiosemicarbazones. * * *", *J. Med. Chem.*, 1974, 17, 172-81. Among the various compounds reported by French et al. in Table I (page 174) may be mentioned 5-acetylamino-2-formylpyridine thiosemicarbazone (compound 49). A variety of compounds were synthesized with 4-position substitutions, as reported by Agrawal et al., "Potential Antitumor Agents. 14. 4-Substituted 2-Formylpyridine Thiosemicarbazones", *J. Med. Chem.*, 1976, 19, 1209-14. This Agrawal et al. research reports on compounds which include 4-dimethylamino-2-formylpyridine thiosemicarbazone (page 1210, compound 5) and 4-piperidino-2-formylpyridine thiosemicarbazone (id., compound 20), 4-pyrrolidinoamino-2-formylpyridine thiosemicarbazone (page 1211, compound 28), 4-bis(hydroxyethyl)amino-2-formylpyridine thiosemicarbazone (id., compound 30) and structurally more remote forms; in no case is there a disclosure of a 2-formylpyridine thiosemicarbazone in this research of Agrawal et al. that has both one of the 4-position substituents and any substituent on the ring other than one example with a 3-methyl group (id., compound 37). French et al. have also made attempts to work in the field with 4-substitution. French et al. disclose only one compound which may be considered to be a (3 or 5)-substituted-4-methyl-2-formylpyridine thiosemicarbazone, i.e., the 3-species, 3-hydroxy-4-methyl-2-formylpyridine thiosemicarbazone, which is compound 51 and which is found to lack "significant activity." Most of the compounds among the 61 tabulated 2-formylpyridine thiosemicarbazones are indicated as possessing "significant activity," which is designated by an asterisk, as explained on page 175. An isomeric form is disclosed, namely, 3-hydroxy-6-methyl-2-formylpyridine thiosemicarbazone, which is compound 52 and which is also found to lack "significant activity."

SUMMARY OF THE INVENTION

In accordance with a first aspect of the invention there are provided compounds of the formula:

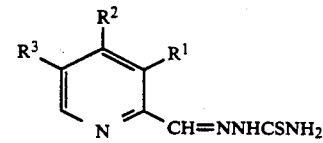

wherein
one of $R^1$ is $NHR^4$ or $NR^4R^5$ or $R^3$ is $NHR^4$, $NR^4R^5$ or OH, and the other is hydrogen;
$R^2$ is hydrogen or $C_{1-4}$ lower alkyl;
$R^4$ is hydrogen, hydroxyl, or $C_{1-4}$ lower alkyl; and
$R^5$ is $C_{1-4}$ lower alkyl.

The term "$C_{1-4}$ lower alkyl" refers to alkyl groups of up to four carbon atoms, methyl, ethyl, propyl and butyl; in accordance with a preferred embodiment, $C_{1-4}$ lower alkyl represents methyl. In one embodiment there are provided compounds wherein $R^4$ is hydrogen. In a further embodiment there are provided compounds wherein $R^2$ is hydrogen. In a further embodiment there are provided compounds wherein $R^2$ is lower alkyl preferably methyl. In accordance with a preferred embodiment, $R^4$ is hydrogen, i.e., the compounds are 3- and 5-amino-2-formylpyridine thiosemicarbazones. The compounds may be free from further substituents in accordance with one embodiment, i.e., $R^2$ is hydrogen, or in a second and also preferred embodiment the compounds of the invention are 3- and 5-amino-4-methyl-2-formylpyridine thiosemicarbazones, i.e., $R^2$ is methyl. Representative compounds of the invention include 3-amino-2-formylpyridine thiosemicarbazone, 5-amino-2-formylpyridine thiosemicarbazone, 3-amino-4-methyl-2-formylpyridine thiosemicarbazone, 5-amino-4-methyl-2-formylpyridine thiosemicarbazone, and 5-hydroxyamino-4-methyl-2-formylpyridine thiosemicarbazone. It is to be understood that any compound of the invention above or any other aspect should be understood as contemplating any pharmaceutically acceptable salts or hydrates thereof.

A method is provided for the treatment of tumors in mammals, e.g., cats, dogs, rats, mice, monkey and man. All of the compounds of the aforementioned first aspect of the invention are specifically considered to be useful in the treatment of tumors. For example, all compounds of the first aspect of the invention are useful in the treatment of the L1210 leukemia in mice. Dosages that are contemplated within the scope of the invention are from about 40 to about 100 mg/kg/day.

In accordance with a second aspect of the invention there is provided a method for the treatment of tumors in mammals, e.g., cats, dogs, rats, mice, monkey and man, which comprises administration of the compounds 3-hydroxy-4-methyl-2-formylpyridine thiosemicarbazone or 5-hydroxy-4-methyl-2-formylpyridine thiosemicarbazone. For example, among tumors which may be treated in accordance with the second aspect of the invention may be mentioned the treatment of the L1210 leukemia in mice. Dosages that are contemplated within the scope of the invention are from about 4 to about 600 mg/kg/day. As part of this second aspect of the invention there is also provided the novel compound 5-hydroxy-4-methyl-2-formylpyridine thiosemicarbazone.

DETAILED DESCRIPTION

The synthesis of the compounds of the first aspect of the invention is described in greater detail in the examples which follow. In general terms, there is first described the synthesis of various 3-amino, 5-amino- and 5-nitro-substituted 2-formylpyridine thiosemicarbazones. Oxidation of 3-nitro-, 5-nitro-, 3-nitro-4-methyl- and 5-nitro-4-methyl-2-picolines with selenium dioxide in refluxing dioxane yielded the corresponding 2-formylpyridines. To reduce the nitro groups to amino functions, the aldehydes were protected by conversion to the cyclic ethylene acetals, which were then reduced by catalytic hydrogenation using Pd/C as a catalyst to give the corresponding amino acetals. The resulting compounds were then reacted with thiosemicarbazide in ethanol containing 10% concentrated hydrochloric acid to form the desired thiosemicarbazone hydrochlorides; the free bases were liberated by treatment with aqueous sodium bicarbonate solution. Condensation of 5-nitro-2-formylpyridine and 5-nitro-4-methyl-2-formylpyridine, with thiosemicarbazide in the presence of hydrochloric acid, followed by treatment with sodium bicarbonate, yielded the corresponding 5-nitro-substituted thiosemicarbazones.

The acetamide and alkylsulfonamide derivatives of 3-amino- and 5-amino-2-formylpyridine thiosemicarbazone were prepared. Acetylation with acetic anhydride in anhydrous pyridine gave acetamide derivatives which were then condensed with thiosemicarbazide to produce 5-acetylamino-2-formylpyridine thiosemicarbazone and 3- and 5-acetylamino-4-methyl-2-formylpyridine thiosemicarbazones. During the process of acidic hydrolysis of the ethylene acetal groups, some hydrolysis of the acetamide functions occurred even though reaction conditions were carefully controlled. The desired pure compounds were obtained by recrystallization from ethanol or by silica gel chromatography. Treatment of 2-(1,3-dioxolanyl)-4-methyl-5-aminopyridine with methanesulfonyl chloride or p-toluenesulfonyl chloride in anhydrous pyridine afforded the corresponding 5-methanesulfonylamino and p-toluenesulfonylamino derivatives, 2-(1,3-dioxolanyl)-4-methyl-5-methanesulfonylaminopyridine and 2-(1,3-dioxolanyl)-4-methyl-5-p-toluenesulfonylaminopyridine, respectively, which were then treated with thiosemicarbazide in the presence of concentrated hydrochloric acid to afford the corresponding 5-methanesulfonylamino- and 5-p-toluenesulfonylamino-4-methyl-2-formylpyridine thiosemicarbazones, 5-methanesulfonylamino-4-methyl-2-formylpyridine thiosemicarbazone and 5-toluenesulfonylamino-4-methyl-2-formylpyridine thiosemicarbazone.

5-Hydroxyamino-4-methyl-2-formylpyridine thiosemicarbazone was synthesized by hydrogenation of 2-(1,3-dioxolanyl)-4-methyl-5-nitropyridine in ethanol using Pd(OH)$_2$/C as a catalyst under 50 psi of hydrogen to yield the 5-hydroxyamino derivative contaminated with about 10–15% of the corresponding 5-amino derivative. 2-(1,3-Dioxolanyl)-4-methyl-5-hydroxyaminopyridine was easily purified by recrystallization from ethanol. The structure was assigned by NMR, mass spectroscopy and elemental analysis. During the reduction process, the rate of absorption of hydrogen decreased considerably after the formation of the 5-hydroxyamino derivative, 2-(1,3-dioxolanyl)-4-methyl-5-hydroxyaminopyridine, and the reaction was terminated at this stage. When the reaction was allowed to proceed until the absorption of hydrogen was complete (about 24 h), however, the 5-amino derivative, 2-(1,3-dioxolanyl)-4-methyl-5-aminopyridine, was obtained in nearly quantitative yield.

Condensation of 2-(1,3-dioxolanyl)-4-methyl-5-hydroxyaminopyridine with thiosemicarbazide in the presence of concentrated hydrochloric acid, followed by treatment with sodium bicarbonate afforded the desired 5-hydroxyamino-4-methyl-2-formylpyridine thiosemicarbazone.

Melting points were determined with a Thomas-Hoover Unimelt apparatus and are uncorrected. $^1$H NMR spectra were recorded on a Varian EM-390 90 MHz NMR spectrometer or a Bruker WM-500 500 MHz spectrometer with Me$_4$Si as the internal reference. The mass spectra (at 70 eV) were provided by the Yale University Chemical Instrumentation Center. TLC was performed on EM precoated silica gel sheets containing a fluorescent indicator. Elemental analyses were carried out by the Baron Consulting Co., Orange, Conn. Where analyses are indicated only by symbols of the elements, the analytical results for those elements were within ±0.4% of the theoretical value.

Use of the compound of the present invention is preferably carried out when the compound is in a pharmaceutically acceptable salt form. Acceptable salts include, for example, inorganic acid salts such as hydrochloride and hydrobromide, organic salts such as acetate, tartrate, citrate, fumarate, maleate, toluenesulfonate, methanesulfonate, ethanesulfonate, hydroxymethanesulfonate, and hydroxyethanesulfonate, metal salts such as sodium salt, potassium salt, calcium salt, and aluminum salt, and salts with a base such as triethylamine salt, guanidine salt, ammonium salt, hydrazine salt, quinine salt, and cinchonine salt. The salts are made using procedures that will be readily apparent to those skilled in the art. Hydrates, which are also contemplated within the scope of the presently claimed invention, can be formulated using principles well known to those of ordinary skill in the art.

The presently claimed invention can be formulated as a pharmaceutical composition in accordance with procedures that will be readily apparent to those of ordinary skill in the art. Preferred pharmaceutical compositions are, for example, tablets, including lozenges and granules, caplets, dragées, pills, gelatin capsules, ampuls, and suppositories comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with a carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

The following examples serve to further illustrate the invention.

EXAMPLE I

A mixture of 3-nitropyridine (1.3 g, 9.4 mmol) and selenium dioxide (1.1 g, 9.4 mmol) in 1,4-dioxane (30 mL), containing 0.8 mL of water, was refluxed under an atmosphere of nitrogen for 20 h. The reaction mixture was cooled and filtered to remove the precipitated black selenium. The filtrate was evaporated in vacuo to dryness and the residue was chromatographed on a silica gel column ($CH_2Cl_2$, $R_f$ 0.82) to afford 0.32 g (23%) of white crystals of 3-nitropyridine-2-carboxaldehyde: mp 61°–62° C. (lit. 63° C.); $^1H$ NMR (90 MHz, $CDCl_3$) δ 7.65 (d, 1H, 5-H, $J_{4,5}=6.0$ Hz, $J_{5,6}=4.5$ Hz), 8.32 (d, 1H, 4-H, $J_{4,5}=6.0$ Hz), 9.05 (d, 1H, 6-H, $J_{5,6}=4.5$ Hz), 10.31 (s, 1H, 2-CHO).

EXAMPLE II

5-Nitropyridine-2-carboxaldehyde was prepared from the nitro derivative, 2-methyl-3-nitropyridine, by the procedure employed for the synthesis of Example I, except that anhydrous dioxane was used as the solvent and the reaction time was 4 h. Yield: 2.0 g (42%); mp 66°–67° C. (lit. 66.5°–67.5° C.); TLC, $R_f$ 0.85 (EtOAc); $^1H$ NMR (90 MHz, $CDCl_3$) δ 8.0 (d, 1H, 3-H, $J_{3,4}=4.5$ HZ), 8.30 (d, 1H, 4-H, $J_{3,4}=4.5$ Hz), 9.25 (s, 1H, 6-H), 10.45 (s, 1H, 2-CHO).

EXAMPLE III

A mixture of 3-nitropyridine-2-carboxaldehyde (1.50 g, 9.70 mmol), ethylene glycol (7 g, 62 mmol) and p-toluenesulfonic acid monohydrate (60 mg, 0.24 mmol) in toluene (150 mL) was refluxed until the starting material was no longer observed by TLC ($CH_2Cl_2$/EtOAc, 4:1, v/v). The reaction mixture was cooled and washed with aqueous sodium bicarbonate solution, water, and brine. The organic layer was dried over $MgSO_4$. The filtrate was evaporated in vacuo to dryness and the residue was chromatographed on a silica gel (120 g) column ($CH_2Cl_2$/EtOAc, 4:1, v/v, $R_f$ 0.50). The product was 2-(1,3-dioxylanyl)-3-nitropyridine, obtained as almost colorless needles (1.65 g, 87%): mp 65°–67° C.; $^1H$ NMR (90 MHz, $CDCl_3$) δ 4.15 (s, 4H, $CH_2CH_2$), 6.52 (s, 1H, 2-CH), 7.52 (m, 1H, 5-H), 8.15 (dd, 1H, 4-H, $J_{4,6}=1$ Hz), 8.85 (dd, 1H, 6-H, $J_{5,6}=4$ Hz, $J_{4,6}=1$ Hz). Anal. ($C_8H_8N_2O_4$) C, H, N.

EXAMPLE IV 2-(1,3-Dioxolanyl)-5-nitropyridine was prepared from 5-nitropyridine-2-carboxaldehyde by the procedure employed for the synthesis of Example III. Yield: 2.0 g (84%); mp 104°–105° C.; TLC $R_f$ 0.73 ($CH_2Cl_2$/EtOAc, 1:1, v/v); 1H NMR (90 MHz, $CDCl_3$) δ 4.10 (s, 4H, $CH_2CH_2$), 5.92 (s, 1H, 2-CH), 7.72 (d, 1H, 3-H, $J_{3,4}=8$ Hz), 8.50 (dd, 1H, 4-H, $J_{3,4}=8$ Hz, $J_{4,6}=2$ Hz), 9.42 (d, 1H, 6-H, $J_{4,6}=2$ Hz). Anal.($C_8H_8N_2O_4$) C, H, N.

EXAMPLE V

A solution of 2-(1,3-dioxolanyl)-3-nitropyridine (1.00 g, 5.1 mmol) in ethanol (100 mL) was hydrogenated overnight in a Parr apparatus at 50 psi of hydrogen in the presence of 10% Pd/C (0.1 g). The reaction mixture was filtered through a Celite-pat and the catalyst was washed with ethanol. The combined filtrate and washings were evaporated in vacuo to dryness and coevaporated with benzene. The resulting solid was recrystallized from benzene to afford 0.81 g (96%) of product, 2-(1,3-dioxolanyl)-3-aminopyridine, as white crystals: mp 73°–74° C.; TLC $R_f$ 0.4 (EtOAc); $^1H$ NMR (90 MHz, $CDCl_3$) δ 4.10 (m, 4H, $CH_2CH_2$), 4.15 (br s, 2H, 3-$NH_2$, $D_2O$ exchangeable), 5.80 (s, 1H, 2-CH), 6.90 (m, 2H, 4-H and 6-H), 7.95 (dd, 1H, 5-H). Anal. ($C_8H_{10}N_2O_2.0.1H_2O$) C, H, N.

EXAMPLE VI 2-(1,3-Dioxolanyl)-5-aminopyridine was prepared from 2-(1,3-dioxolanyl)-5-nitropyridine by the procedure employed in Example V. Yield: 2.6 g (93%); mp 81°–82° C.; TLC $R_f$ 0.18 (EtOAc); $^1H$ NMR (90 MHz, $CDCl_3$) δ 3.85 (br s, 2H, 5-$NH_2$, $D_2O$ exchangeable), 4.05 (m, 4H, $CH_2CH_2$), 5.72 (s, 1H, 2-CH), 6.95 (dd, 1H, 4-H, $J_{3,4}=8$ Hz, $J_{4,6}=2$ Hz), 7.30 (d, 1H, 3-H, $J_{3,4}=8$ Hz) 8.08 (d, 1H, 6-H, $J_{4,6}=2$ Hz). Anal. ($C_8H_{10}N_2O_2$) C, H, N.

EXAMPLE VII

To a solution of 2-(1,3-dioxolanyl)-3-aminopyridine (0.80 g, 4.8 mmol) in 10 mL of ethanol, 8 mL of water and 2 mL of concentrated hydrochloric acid was added 0.48 g (5.3 mmol) of thiosemicarbazide. The mixture was stirred at room temperature overnight and refluxed for 1 h, cooled and filtered. The crude yellow hydrochloride salt was dissolved in 50 mL of hot water and filtered. To the hot filtrate was added 10 mL of 5% sodium bicarbonate solution. The mixture was stirred at room temperature for 1 h, filtered and washed with water, followed by ethanol to yield 3-amino-2-formylpyridine thiosemicarbazone. Yield: 0.72 g (77%); mp 240°–241° C. dec; MS m/e 194 (M+); $^1H$ NMR (90 MHz, DMSO-$d_6$) δ 6.48 (br s, 2H, 3-$NH_2$, $D_2O$ exchangeable), 7.12 (m, 2H, 4-H and 6-H), 7.83 (dd, 1H, 5-H), 8.10 (br s, 2H, $CSNH_2$, $D_2O$ exchangeable), 8.10 (s, 1H, 2-CH), 10.95 (s, 1H, NNH, $D_2O$ exchangeable). Anal. ($C_7H_9N_5S$) C, H, N.

EXAMPLE VIII

5-Amino-2-formylpyridine thiosemicarbazone was prepared from 2-(1,3-dioxolanyl)-5-aminopyridine by the procedure employed for the synthesis of Example VII. Yield: 1.9 g (82%); mp 205°–207° C.; MS m/e 194 (M+); $^1H$ NMR (DMSO-$d_6$, 500 MHz) δ 5.60 (br s, 2H, 3-$NH_2$, $D_2O$ exchangeable), 6.95 (dd, 1H, 4-H, $J_{3,4}=8$ Hz, $J_{4,6}=1.5$ Hz), 7.65 (s, 1H, 2-CH), 7.75 (d, 1H, 6-H, $J_{4,6}=1.5$ Hz), 7.90 (d, 1H, 3-H, $J_{3,4}=8$ Hz), 7.85 and 8.10 (two br s, 2H, $CSNH_2$, $D_2O$ exchangeable), 11.05 (s, 1H, NNH, $D_2O$ exchangeable). Anal. ($C_7H_9N_5S.0.4H_2O$) C, H, N.

EXAMPLE IX

3-Amino-4-methyl-2-formylpyridine thiosemicarbazone was prepared from 2-(1,3-dioxolanyl)-4-methyl-3-aminopyridine by the procedure employed for the synthesis of Example VII. Yield: 0.5 g (76%); mp 227°–228° C.; MS m/e 208 (M+); $^1$H NMR (500 MHz, DMSO-$d_6$) δ 2.25 (s, 3H, 4-CH$_3$), 6.18 (s, 2H, 3-NH$_2$, D$_2$O exchangeable), 7.01 (d, 1H, 5-H, J$_{5,6}$=6 Hz), 7.78 (d, 1H, 6-H, J$_{5,6}$=6 Hz), 7.90 (s, 2H, CSNH$_2$, D$_2$O exchangeable), 8.32 (s, 1 H, 2-CH), 11.31 (s, 1H, NNH, D$_2$O exchangeable). Anal. (C$_8$H$_{11}$N$_5$S.HCl.H$_2$O) C, H, N.

EXAMPLE X

5-Amino-4-methyl-2-formylpyridine thiosemicarbazone was prepared from 2-(1,3-dioxolanyl)-4-methyl-5-aminopyridine by the procedure employed for the synthesis of Example VII. Yield: 0.64 g (78%); mp 235°–236° C.; MS m/e 208 (M+); $^1$H NMR (500 MHz, DMSO-$d_6$) δ 2.10 (s, 3H, 4-CH$_3$), 5.48 (s, 2H, 5-NH$_2$, D$_2$O exchangeable), 7.80 (s, 2H, CSNH$_2$, D$_2$O exchangeable), 7.80 (s, 1H, 3-H), 7.95 (s, 1H, 6-H), 8.00 (s, 1H, 2-CH), 11.50 (s, 1H, NNH, D$_2$O exchangeable). Anal. (C$_8$H$_{11}$N$_5$S.HCl.H$_2$O) C, H, N.

EXAMPLE XI

A mixture of 5-nitropyridine-2-carboxaldehyde (0.50 g, 3.3 mmol) and thiosemicarbazide (0.36 g, 4 mmol) in 20 mL of 70% aqueous ethanol solution was refluxed for 2 h, cooled and filtered. The yellow precipitate that formed was washed with water and recrystallized from ethanol to give 0.54 g (73%) of product, 5-nitro-2-formylpyridine thiosemicarbazone: mp 215°–217° C.; $^1$H NMR (90 MHz, DMSO-$d_6$) δ 8.25 (d, 1H, 3-H), 8.35 and 8.55 (two br s, 2H, CSNH$_2$, D$_2$O exchangeable), 8.90 (dd, 1H, 4-H), 9.75 (d, 1H, 6-H), 10.15 (s, 1H, 2-CH), 11.95 (s, 1H, NNH, D$_2$O exchangeable). Anal. (C$_7$H$_7$N$_5$O$_2$S) C, H, N.

EXAMPLE XII

5-Nitro-4-methyl-2-formylpyridine thiosemicarbazone was prepared from 4-methyl-5-nitropyridine-2-carboxaldehyde by the procedure employed for the synthesis of Example XI. Yield: 0.38 g (88%); mp 220°–222° C.; $^1$H NMR (90 MHz, DMSO-$d_6$) δ 2.55 (s, 3H, 4-CH$_3$), 8.12 (s, 1H, 3-H), 8.30 and 8.50 (two br s, 2H, CSNH$_2$, D$_2$O exchangeable), 9.15 (s, 1H, 6-H), 9.45 (s, 1H, 2-CH), 11.85 (s, 1H, NNH, D$_2$O exchangeable). Anal. (C$_8$H$_9$N$_5$O$_2$S) C, H, N.

EXAMPLE XIII

To a stirred solution of 2-(1,3-dioxolanyl)-5-aminopyridine (2.0 g, 12 mmol) in 15 mL of anhydrous pyridine in an ice bath was added dropwise 2 mL of acetic anhydride at 0.5° C. The reaction mixture was stirred overnight and evaporated in vacuo to dryness. The residue was co-evaporated with ethanol (10 mL) and recrystallized from ethanol to yield 2.1 g (82%) of product, 2-(1,3-dioxolanyl)-5-acetylaminopyridine: mp 145°–147° C.; $^1$H NMR (90 MHz, CDCl$_3$) δ 2.05 (s, 3H, CH$_3$), 4.10 (m, 4H, CH$_2$CH$_2$), 5.82 (s, 1H, 2-CH), 7.10 (dd, 1H, 4-H, J$_{3,4}$=8 Hz, J$_{4,6}$=2 Hz), 7.45 (d, 1H, 3-H, J$_{3,4}$=8 Hz), 8.40 (br s, 1H, NH, D$_2$O exchangeable), 8.68 (d, 1H, 6-H, J$_{4,6}$=2 Hz). Anal. (C$_{10}$H$_{12}$N$_2$O$_3$) C, H, N.

EXAMPLE XIV

A mixture of 2-(1,3-dioxolanyl)-4-methyl-3-aminopyridine (500 mg, 2.78 mmol), 5 mL of acetic anhydride and 15 mL of anhydrous pyridine was refluxed overnight and evaporated in vacuo to dryness. The residue was dissolved in CH$_2$CH$_2$ (30 mL), washed with 10% sodium bicarbonate, brine, and water, then dried (anhydrous MgSO$_4$). The solvent was removed and the residue was purified on a silica gel column (CH$_2$Cl$_2$/CH$_3$OH, 10:1, v/v, R$_f$ 0.67) to produce 440 mg (72%) of product, 2-(1,3-dioxolanyl)-4-methyl-3-acetylaminopyridine: mp 77°–79° C., $^1$H NMR (90 MHz, CDCl$_3$) δ 2.10 (s, 3H, COCH$_3$), 2.17 (s, 3H, 4-CH$_3$), 2.20 (br s, 1H, NH, D$_2$O exchangeable), 3.95 (m, 4H, CH$_2$CH$_2$), 5.70 (s, 1H, 2-CH), 7.15 (d, 1H, 5-H, J$_{5,6}$=6 Hz), 8.42 (d, 1H, 6-H, J$_{5,6}$=6 Hz). Anal. (C$_{11}$H$_{14}$N$_2$O$_3$) C, H, N.

EXAMPLE XV 2-(1,3-Dioxolanyl)-4-methyl-5-acetylaminopyridine was prepared from 2-(1,3-dioxolanyl)-4-methyl-5-aminopyridine by the procedure employed for the synthesis of Example XIV. Yield: 0.5 g (82%); mp 98°–99° C.; TLC, R$_f$ 0.65 (CH$_2$Cl$_2$/EtOH, 10:1, v/v); $^1$H NMR (90 MHz, CDCl$_3$) δ 2.08 (s, 3H, COCH$_3$), 2.15 (s, 3H, 4-CH$_3$), 4.05 (m, 4H, CH$_2$CH$_2$), 5.72 (s, 1H, 2-CH), 7.30 (s, 1H, 3-H), 8.05 (br s, 1H, NH, D$_2$O exchangeable), 8.58 (s, 1H, 6-H). Anal. (C$_{11}$H$_{14}$N$_2$O$_3$) C, H, N.

EXAMPLE XVI

A mixture of 2-(1,3-dioxolanyl)-5-acetylaminopyridine (0.60 g, 3.6 mmol), thiosemicarbazide (0.40 g, 4.4 mmol), 1 mL of glacial acetic acid and 10 mL of ethanol was heated with stirring at 50° C. for 6 h, cooled and filtered. The acetic acid salt was dissolved in hot water, filtered into 15 mL of 5% sodium bicarbonate solution and the mixture was stirred at room temperature for 1 h. The yellow precipitate that formed was filtered, washed with water, and recrystallized from ethanol twice to give 0.46 g (54%) of product, 5-acetylamino-2-formylpyridine thiosemicarbazone: mp 215°–217° C.; $^1$H NMR (90 MHz, DMSO-$d_6$) δ 2.05 (s, 3H, COCH$_3$), 8.00 (m, 3H, 2-CH, 3-H and 4-H), 8.05 and 8.15 (two br s, 2H, CSNH$_2$, D$_2$O exchangeable), 8.80 (d, 1H, 6-H, J$_{4,6}$=1.5 Hz), 10.30 (s, 1H, 5-NH, D$_2$O exchangeable), 11 30 (s, 1H, NNH, D$_2$O exchangeable). Anal. (C$_9$H$_{11}$N$_5$OS) C, H, N.

EXAMPLE XVII

A mixture of 2-(1,3-dioxolanyl)-4-methyl-3-acetylaminopyridine (0.41 g, 1.9 mmol), thiosemicarbazone (0.2 g, 2.2 mmol), 1 mL of concentrated hydrochloric acid and 10 mL of ethanol was stirred at room temperature overnight. The yellow precipitate (hydrochloride salt) that formed was filtered and washed with water, followed by ethanol. The hydrochloride salt was dissolved in hot water and stirred with 10 mL of 5% sodium bicarbonate solution for 1 h, filtered, and washed with water. The crude product was chromatographed on a silica gel column (CH$_2$Cl$_2$/CH$_3$OH, 4:1, v/v, R$_f$ 0.52) to give 0.21 g (45%) of product, 3-acetylamino-4-methyl-2-formylpyridine thiosemicarbazone: mp 225°–227° C.; $^1$H NMR (90 MHz, DMSO-$d_6$) δ 2.05 (s, 3H, COCH$_3$), 2.18 (s, 3H, 4-CH$_3$), 7.30 (d, 1H, 5-H, J$_{5,6}$=6 Hz), 8.14 (d, 1H, 2-CH), 7.90 and 8.30 (two br s, 2H, CSNH$_2$, D$_2$O exchangeable), 8.35 (d, 1H, 6-H, J$_{5,6}$=6 Hz), 9.71 (s, 1H, 3-NH, D$_2$O exchangeable), 11.53 (s, 1H, NNH, D$_2$O exchangeable). Anal. (C$_{10}$H$_{13}$N$_5$OS) C, H, N.

EXAMPLE XVIII

5-Acetylamino-4-methyl-2-formylpyridine thiosemicarbazone was prepared from 2-(1,3-dioxolanyl)-4-methyl-5-acetylaminopyridine by the procedure employed for the synthesis of Example XVII. Yield: 0.42 g (76%); mp 229°–231° C.; TLC, R$_f$ 0.52 (CH$_2$Cl$_2$/CH$_3$OH, 4:1, v/v); $^1$H NMR (90 MHz, DMSO-d$_6$) δ 2.10 (s, 3H, COCH$_3$), 2.25 (s, 3H, 4-CH$_3$), 7.90 (s, 1H, 3-H), 8.05 (s, 1H, 2-CH), 8.05 and 8.35 (two br s, 2H, CSNH$_2$, D$_2$O exchangeable), 8.60 (s, 1H, 6-H), 9.62 (s, 1H, 5-NH, D$_2$O exchangeable), 11.60 (s, 1H, NNH, D$_2$O exchangeable). Anal. (C$_{10}$H$_{13}$N$_5$OS) C, H, N.

EXAMPLE XIX

To a stirred solution of 2-(1,3-dioxolanyl)-4-methyl-5-aminopyridine (0.8 g, 4.4 mmol) in 10 mL of anhydrous pyridine in an ice bath was added dropwise 0.6 g (5.3 mmol) of methanesulfonyl chloride at 0°–5° C. The mixture was stirred at room temperature overnight and evaporated in vacuo to dryness. The residue was co-evaporated with toluene (10 mL) and then partitioned between CH$_2$CH$_2$ (30 mL) and water (10 mL). The organic layer was washed with 10% sodium bicarbonate, brine and water, dried with anhydrous MgSO$_4$, and filtered. The filtrate was concentrated to a small volume and purified on a silica gel column (EtOAc, R$_f$0.40) to give 0.68 g of product, 2-(1,3-dioxolanyl)-4-methyl-5-methanesulfonylaminopyridine: mp 128°–130° C.; $^1$H NMR (90 MHz, CDCl$_3$) δ 2.40 (s, 3H, 4-CH$_3$), 3.03 (s, 3H, CH$_3$SO), 4.12 (m, 4H, CH$_2$CH$_2$), 5.65 (s, 1H, 2-CH), 7.40 (s, 1H, 3-H), 8.10 (br s, 1H, NH, D$_2$O exchangeable), 8.52 (s, 1H, 6-H). Anal. (C$_{10}$H$_{14}$N$_2$O$_4$S) C, H, N.

EXAMPLE XX 2-(1,3-Dioxolanyl)-4-methyl-5-p-toluenesulfonylaminopyridine was prepared from 2-(1,3-dioxolanyl)-4-methyl-5-aminopyridine by a procedure similar to that employed in Example XIX. Yield: 0.75 g (77%); mp 155°–156° C.; $^1$H NMR (90 MHz, CDCl$_3$) δ 2.05 (s, 3H, ArCH$_3$), 2.32 (s, 3H, 4-CH$_3$), 4.10 (m, 4H, CH$_2$CH$_2$), 5.70 (s, 1H, 2-CH), 6.50 (br s, 1H, NH, D$_2$O exchangeable), 7.20–7.40 (m, 5H, ArH and 3-H), 8.20 (s, 1H, 6-H). Anal. (C$_{16}$H$_{18}$N$_2$O$_4$S) C, H, N.

EXAMPLE XXI

A mixture of 2-(1,3-dioxolanyl)-4-methyl-5-methanesulfonylaminopyridine (0.93 g, 3.6 mmol), thiosemicarbazide (0.37 g, 4.0 mmol) and 10 mL of 5% hydrochloric acid solution was heated with stirring at 60° C. for 4 h and cooled. The yellow precipitate (hydrochloride salt) that formed was filtered and washed with a small amount of water. The hydrochloride salt was then stirred in 10 mL of 1 N NaOH solution for 30 min and filtered. The filtrate was neutralized with dilute acetic acid, filtered, washed with water followed by ethanol to give 0.65 g (63%) of product, 5-methanesulfonylamino-4-methyl-2-formylpyridine thiosemicarbazone: mp 210°–212° C.; $^1$H NMR (90 MHz, DMSO-d$_6$) δ 2.35 (s, 3H, 4-CH$_3$), 3.05 (s, 3H, 4-CH$_3$SO), 8.05 (s, 1H, 3-H), 8.22 (s, 1H, 6-H), 8.30 (s, 1H, 2-CH), 8.15 and 8.35 (two br s, 2H, CSNH$_2$, D$_2$O exchangeable), 9.45 (br s, 1H, SO$_2$NH, D$_2$O exchangeable), 11.45 (s, 1H, NNH, D$_2$O exchangeable). Anal. (C$_9$H$_{13}$N$_5$O$_2$S$_2$.0.75 H$_2$O) C, H, N.

EXAMPLE XXII

5-Toluenesulfonylamino-4-methyl-2-formylpyridine thiosemicarbazone was prepared from 2-(1,3-dioxolanyl)-4-methyl-5-p-toluenesulfonylaminopyridine by the procedure employed for the synthesis of Example XXI. Yield: 0.43 g (80%); mp 234°–236° C.; $^1$H NMR (90 MHz, DMSO-d$_6$) δ 2.12 (s, 3H, ArCH$_3$), 2.40 (s, 3H, 4-CH$_3$), 7.30–7.40 (m, 4H, ArH), 8.05 (s, 1H, 3-H), 8.20 (s, 1H, 6-H), 8.30 (s, 1H, 2-CH), 8.35 and 8.55 (two br s, 2H, CSNH$_2$, D$_2$O exchangeable), 9.40 (br s, 1H, SO$_2$NH, D$_2$O exchangeable), 11.55 (s, 1H, NNH, D$_2$O exchangeable). Anal. (C$_{15}$H$_{17}$N$_5$O$_2$S$_2$) C, H, N.

EXAMPLE XXIII

A solution of 2-(1,3-dioxolanyl)-4-methyl-5-nitropyridine (1.8 g, 8.6 mmol) in ethanol (100 mL) was hydrogenated for 2 h in a Parr apparatus at 50 psi of hydrogen in the presence of 20% Pd(OH)$_2$/C (0.2 g). The reaction mixture was filtered through a Celite-pat and the catalyst was washed with ethanol. The combined filtrate and washings were evaporated in vacuo to dryness. The residue was recrystallized from ethanol twice to give 1.0 g (60%) of product: mp 180°–181° C. as white crystals of 2-(1,3-dioxolanyl)-4-methyl-5-hydroxyaminopyridine; MS m/e 167 (M$^+$+1); $^1$H NMR (500 MHz, DMSO-d$_6$) δ 2.08 (s, 3H, 4-CH$_3$), 3.90–4.05 (m, 4H, CH$_2$CH$_2$), 5.54 (s, 1H, 2-CH), 7.13 (s, 1H, 3-H), 8.18 (s, 1H, 6-H), 8.29 (s, 1H., NH, D$_2$O exchangeable), 8.45 (s, 1H, OH, D$_2$O exchangeable). Anal. (C$_9$H$_{12}$N$_2$O$_3$) C, H, N.

EXAMPLE XXIV

5-Hydroxyamino-4-methyl-2-formylpyridine thiosemicarbazone was prepared from 2-(1,3-dioxolanyl)-4-methyl-5-hydroxyaminopyridine by the procedure employed for the synthesis of Example VII. Yield: 0.45 g (77%); mp 197°–198° C.; MS m/e 224 (M$^+$); $^1$H NMR (90 MHz, DMSO-d$_6$) δ 2.35 (s, 3H, 4-CH$_3$), 8.12 (m, 3H, 3-H, 6-H and 2-CH), 8.55 and 8.75 (two br s, 2H, CSNH$_2$, D$_2$O exchangeable), 9.15 (br s, 2H, HONH, D$_2$O exchangeable), 12.10 (s, 1H, NNH, D$_2$O exchangeable). Anal. (C$_8$H$_{11}$N$_5$OS) C, H, N.

The following discussion relates to the biological activities of the compounds of the first aspect of the invention represented by the experimental work of Examples I–XXIV.

The tumor-inhibitory properties of the substituted 2-formylpyridine thiosemicarbazones measuring their effects on the survival time of mice baring the L1210 leukemia.

EXAMPLE XXV

5-Hydroxy-2-formylpyridine thiosemicarbazone was used as a standard for comparison with the compounds of the invention which are tested in the following examples. The 5-hydroxy-2-formylpyridine thiosemicarbazone was administered by intraperitoneal injection, beginning 24 hours after tumor implantation with the maximum effective daily dosage being 40 mg/kg. Administration was once per day for a total of six consecutive days to a representative sample population. (The number of mice tested was in the amount of 5–10 per dosage level). The average percentage change in body weight from onset to termination of the therapy was +2.0. A value T/C×100 is calculated, which is the ratio of the survival time of treated to control animals×100, which was determined to be 133.

It is noted that while a value of 133 was obtained, in reports by French et al., supra, a value of 268 was reported. The difference may be due to the L1210 leukemia cell lines employed or differences in the schedule of drug administration. Although the compound was administered by intraperitoneal injection starting 24 h after tumor inoculation both in this Example and in the French et al. study, the present Example employed six daily treatments, while French et al. used daily treatments, continued until half the test animals were dead.

EXAMPLE XXVI

3-Amino-2-formylpyridine thiosemicarbazone was administered by intraperitoneal injection to mice bearing the L1210 leukemia, beginning 24 hours after tumor implantation, with the maximum effective daily dosage being 40 mg/kg. Administration was once per day for a total of six consecutive days to a representative sample population. (The number of mice tested was in the amount of 5–10 per dosage level). The average percentage change in body weight from onset to termination of the therapy was −5.9. A value T/C×100 is calculated, which is the ratio of the survival time of treated to control animals×100, and has a value of 187, which compares favorably with the value for the reference standard used in the test in Example XXV, 5-hydroxy-2-formylpyridine thiosemicarbazone, which has a value of 133.

EXAMPLE XXVII

5-Amino-2-formylpyridine thiosemicarbazone was administered by intraperitoneal injection to mice bearing the L1210 leukemia, beginning 24 hours after tumor implantation, with the maximum effective daily dosage being 20 mg/kg. Administration was once per day for a total of six consecutive days to a representative sample population. (The number of mice tested was in the amount of 5–10 per dosage level). The average percentage change in body weight from onset to termination of the therapy was −2.8. A value T/C×100 is calculated, which is the ratio of the survival time of treated to control animals×100, and has a value of 140, which compares favorably with the value for the reference standard used in the test in Example XXV, 5-hydroxy-2-formylpyridine thiosemicarbazone, which has a value of 133.

EXAMPLE XXVIII

3-Amino-4-methyl-2-formylpyridine thiosemicarbazone was administered by intraperitoneal injection to mice bearing the L1210 leukemia, beginning 24 hours after tumor implantation, with the maximum effective daily dosage being 20 mg/kg. Administration was once per day for a total of six consecutive days to a representative sample population. (The number of mice tested was in the amount of 5–10 per dosage level). The average percentage change in body weight from onset to termination of the therapy was −2.8. A value T/C×100 is calculated, which is the ratio of the survival time of treated to control animals×100, and has a value of 190, which compares favorably with the value for the reference standard used in the test in Example XXV, 5-hydroxy-2-formylpyridine thiosemicarbazone, which has a value of 133.

EXAMPLE XXIX

5-Amino-4-methyl-2-formylpyridine thiosemicarbazone was administered by intraperitoneal injection to mice bearing the L1210 leukemia, beginning 24 hours after tumor implantation, with the maximum effective daily dosage being 20 mg/kg. Administration was once per day for a total of six consecutive days to a representative sample population. (The number of mice tested was in the amount of 5–10 per dosage level). The average percentage change in body weight from onset to termination of the therapy was −7.0. A value T/C×100 is calculated, which is the ratio of the survival time of treated to control animals×100, and has a value of 138, which compares favorably with the value for the reference standard used in the test in Example XXV, 5-hydroxy-2-formylpyridine thiosemicarbazone, which has a value of 133.

EXAMPLE XXX

5-Hydroxyamino-4-methyl-2-formylpyridine thiosemicarbazone was administered by intraperitoneal injection to mice bearing the L1210 leukemia, beginning 24 hours after tumor implantation, with the maximum effective daily dosage being 10 mg/kg. Administration was once per day for a total of six consecutive days to a representative sample population. (The number of mice tested was in the amount of 5–10 per dosage level). The average percentage change in body weight from onset to termination of the therapy was −2.7. A value T/C×100 is calculated, which is the ratio of the survival time of treated to control animals×100, and has a value of 136, which compares favorably with the value for the reference standard used in the test in Example XXV, 5-hydroxy-2-formylpyridine thiosemicarbazone, which has a value of 133.

The following examples relate to the second aspect of the invention:

EXAMPLES XXXI-XXXII

Fuming sulfuric acid (1500 g, 15.3 mol) was added slowly to 2,4-lutidine (165 mL, 1.43 mol) and cooled in an ice bath with stirring. Potassium nitrate (262.5 g, 2.60 mol) was then added slowly. The reaction mixture was gradually heated to 100° C. and maintained at this temperature for 8 h. The reaction mixture was then heated at 120° C. for an additional 8 h. After cooling to room temperature, the reaction mixture was poured onto ice (2.5 kg). The solution was neutralized to pH 7 using potassium carbonate and extracted with chloroform (3×4 L). The organic layer was dried over anhydrous $Na_2SO_4$ and the solvent was evaporated; the remaining solution was distilled under reduced pressure. 3-Nitro-2,4-dimethylpyridine (41.71 g, 0.27 mol, 19%, 37° C./0.24 mm Hg), 5-nitro-2,4-dimethylpyridine (38.18 g, 0.25 mol, 18%, 44° C./0.17 mm Hg) and a mixture of 3- and 5-nitro-2,4-dimethylpyridine (13.74 g, 0.09 mol) were obtained. 3-Nitro-2,4-dimethylpyridine: $^1H$ NMR (90 MHz, $CDCl_3$) δ 2.33 (s, 3H, 4-$CH_3$), 2.53 (s, 3H, 2-$CH_3$), 7.02 (d, 1H, 5-H, $J_{5,6}$=4.5 Hz), 8.35 (d, 1H, 6-H, $J_{5,6}$=4.5 Hz). 5-Nitro-2,4-dimethylpyridine: $^1H$ NMR (90 MHz, $CDCl_3$) δ 2.70 (s, 6H, 2- and 4-$CH_3$), 7.17 (s, 1H, 3-H), 9.10 (s, 1H, 6-H).

EXAMPLE XXXIII

To a solution of 3-nitro-2,4-dimethylpyridine of Example XXXI (31.4 g, 0.21 mol) in 200 mL of absolute ethanol was added 5% Pd-C (2 g). The mixture was hydrogenated under 59 psi of pressure for 2 h. The solution was filtered and the solvent was evaporated in vacuo to give a solid (24.0 g, 98%): mp 48°–50° C. (lit. 51°–53° C.). The product, 3-amino-2,4-dimethylpyridine, appeared homogeneous on TLC and by NMR analysis and was used without further purification. $^1$H NMR (90 MHz, CDCl$_3$) δ 2.17 (s, 3H, 4-CH$_3$), 2.33 (s, 3H, 2-CH$_3$), 3.60 (s, 2H, 3-NH$_2$, D$_2$O exchangeable), 6.85 (d, 1H, 5-H, J$_{5,6}$=4.5 Hz), 7.85 (d, 1H, 6-H, J$_{5,6}$=4.5 Hz).

EXAMPLE XXXIV

5-Amino-2,4-dimethylpyridine was synthesized by methodology used for Example XXXIII except that the starting material was 5-nitro-2,4-dimethylpyridine. Yield: 24.1 g (98%); mp 62°–64° C. (lit. 66°–68° C.); $^1$H NMR (90 MHz, CDCl$_3$) δ 2.10 (s, 3H, 4-CH$_3$), 2.37 (s, 3H, 2-CH$_3$), 3.33 (s, 2H, 3-NH$_2$, D$_2$O exchangeable), 6.70 (s, 1H, 3-H), 7.79 (s, 1H, 6-H).

EXAMPLE XXXV

To a solution of 3-amino-2,4-dimethylpyridine (25.0 g, 0.21 mol) in 10% sulfuric acid (405 mL) cooled to 0° C. by dry ice in acetone with stirring, a solution of sodium nitrite (16.2 g, 0.23 mol) in 160 mL of water was added dropwise at 0.5° C. over a period of 7 min. The solution was maintained at 0° C. for an additional 15 min and then heated in a steam-bath for 15 min. After cooling to room temperature, the solution was neutralized with K$_2$CO$_3$ to pH 7. The product was then extracted with chloroform (3×500 mL). The organic layer was dried over anhydrous Na$_2$SO$_4$ and the solvent was removed in vacuo. The product was recrystallized from acetone, and the mother liquid was purified by silica gel column chromatography (EtOAc) to afford an additional amount of the pure product, 3-hydroxy-2,4-dimethylpyridine. The total yield was 12.7 g (51%) as a colorless solid: mp 105°–106° C. (lit. 99°–101° C.); $^1$H NMR (90 MHz, CDCl$_3$) δ 2.25 (s, 3H, 4-CH$_3$), 2.50 (s, 3H, 2-CH$_3$), 6.97 (d, 1H, 5-H, J$_{5,6}$=4.5 Hz), 7.95 (d, 1H, 6-H, J$_{5,6}$=4.5 Hz), 11.20 (s, 1H, 5-OH, D$_2$O exchangeable).

EXAMPLE XXXVI

5-Hydroxy-2,4-dimethylpyridine was synthesized by methodology used for Example XXXV except that the starting material was 5-amino-2,4-dimethylpyridine. Yield: 12.6 g (51%) as a colorless solid; mp 146°–148° C. (lit. 144°–146° C.); $^1$H NMR (90 MHz, CDCl$_3$) δ 2.20 (s, 3H, 4-CH$_3$), 2.47 (s, 3H, 2-CH$_3$), 6.87 (s, 1H, 3-H), 7.97 (s, 1H, 6-H), 11.43 (s, 1H, 5-OH, D$_2$O exchangeable).

EXAMPLE XXXVII

To a stirred solution of 3-hydroxy-2,4-dimethylpyridine (23.7 g, 0.19 mol) in 130 mL of glacial acetic acid was added dropwise 36 mL of 30% hydrogen peroxide. The reaction mixture was heated to 80° C. and two additional portions of 30% hydrogen peroxide (36 mL) were added at 3 h intervals. The solution was maintained at 80° C. for a total of 9 h and the solvent was removed under reduced pressure. The residue was purified by silica gel column chromatography (EtOAc-MeOH, 7:3, v/v) to give 10.3 g (38%) of product, 3-hydroxy-2,4-dimethylpyridine-N-oxide: mp 134°–136° C.; $^1$H NMR (90 MHz, Me$_2$SO-d$_6$) δ 2.17 (s, 3H, 4-CH$_3$), 2.32 (s, 3H, 2-CH$_3$), 6.94 (d, 1H, 5-H, J$_{5,6}$=6 Hz), 7.72 (s, 1H, 6-H, J$_{5,6}$=6 Hz); HRMS (FAB) m/z cacld. for C$_7$H$_9$NO$_2$ 140.0711, found 140.0707. Anal. (C$_7$H$_9$NO$_2$) C, H, N.

EXAMPLE XXXVIII

5-Hydroxy-2,4-dimethylpyridine-N-oxide was synthesized by methodology used for Example XXXVII except that the starting material was 5-hydroxy-2,4-dimethylpyridine. Yield: 10.0 g (37%); mp 229° C. dec; $^1$H NMR (90 MHz, Me$_2$SO-d$_6$) δ 2.10 (s, 3H, 4-CH$_3$), 2.22 (s, 3H, 2-CH$_3$), 7.07 (s, 1H, 3-H), 7.70 (s, 1H, 6-H); HRMS (FAB) m/z cacld. for C$_7$H$_9$NO$_2$ 140.0711, found 140.0722.

EXAMPLE XXXIX

A mixture of 3-hydroxy-2,4-dimethylpyridine-N-oxide (11.3 g, 81 mmol) and acetic anhydride (200 mL) was heated at 110° C. with stirring for 2.5 h. After cooling, the solvent was evaporated under reduced pressure and the residue was purified by silica gel column chromatography (EtOAc-hexane, 1:1, v/v) to yield 13.5 g (74%) of product, 3-acetoxy-4-methyl-2-acetoxymethylpyridine, as a slightly yellow oil. $^1$H NMR (90 MHz, CDCl$_3$) δ 2.20 (s, 3H, 4-CH$_3$), 2.37 (s, 6H, 2-OCOCH$_3$), 5.17 (s, 2H, 2-CH$_2$), 7.15 (d, 1H, 5-H, J$_{5-6}$=4.5 Hz), 8.35 (d, 1H, 6-H, J$_{5-6}$=4.5 Hz); HRMS (FAB) m/z cacld. for C$_{11}$H$_{13}$NO$_4$ 224.0923, found 224.0935. Anal. (C$_{11}$H$_{13}$NO$_4$) C, H, N.

EXAMPLE XL

5-Acetoxy-4-methyl-2-acetoxymethylpyridine was synthesized by methodology used for Example XXXIX except that the starting material was 5-hydroxy-2,4-dimethylpyridine-N-oxide. Yield: 9.85 g (54%) as a yellow oil. $^1$H NMR (90 MHz, CDCl$_3$) δ 2.15 and 2.25 (two s, 6H, 2-OCOCH$_3$), 2.35 (s, 3H, 4-CH$_3$), 5.13 (s, 2H, 2-CH$_2$), 7.23 (s, 1H, 3-H), 8.23 (s, 1H, 6-H); HRMS (FAB) m/z cacld. for C$_{11}$H$_{13}$NO$_4$ 224.0923, found 224.0943. Anal. (C$_{11}$H$_{13}$NO$_4$) C, H, N.

EXAMPLE XLI

To a solution of 3-acetoxy-4-methyl-2-acetoxymethylpyridine (13.5 g, 60 mmol) in 74 mL of glacial acetic acid was added dropwise with stirring 21 mL of 30% hydrogen peroxide. The mixture was heated to 80° C. and two additional portions of 30% hydrogen peroxide (21 mL) was added at 3 h intervals. The solution was maintained at 80° C. for a total of 9 h. The solvent was evaporated in vacuo and the residue was purified by silica gel column chromatography (EtOAc-MeOH, 7:3, v/v) to give 2.62 g (18%) of product, 3-acetoxy-4-methyl-2-acetoxymethylpyridine-N-oxide: mp >360° C. The product was used immediately for the next step.

EXAMPLE XLII

A mixture of 3-acetoxy-4-methyl-2-acetoxymethylpyridine-N-oxide (2.77 g, 11.6 mmol) and 54 mL of acetic anhydride was heated with stirring at 110° C. for 2.5 h. After cooling, the solvent was evaporated under reduced pressure and the residue was purified by silica gel column chromatography (EtOAc-hexane, 1:1, v/v) to yield 1.54 g (47%) of product, 3-acetoxy-4-methyl-2-diacetoxymethylpyridine, as a yellow oil: $^1$H NMR (90 MHz, CDCl$_3$) δ 2.10–2.40 (m, 12H, 2-C(OCOCH$_3$)$_2$, 3-OCOCH$_3$ and 4-CH$_3$), 5.17 (s, 2H, 2-CH$_2$), 7.20–7.38 (m, 1H, 5-H), 8.37–8.52(m, 1H, 6-H); HRMS (FAB) m/z cacld. for C$_{13}$H$_{15}$NO$_6$ 282.0978, found 282.0990. Anal. (C$_{13}$H$_{15}$NO$_6$) C, H, N.

EXAMPLE XLIII

To a slurry of thiosemicarbazide (0.26 g, 2.9 mmol) in 5 mL of conc. HCl and 15 mL of ethanol was added a solution of 3-acetoxy-4-methyl-2-diacetoxymethylpyridine (0.8 g, 2.9 mmol) in 10 mL of ethanol. The reaction mixture was stirred at 50° C. for 2 h and the precipitate was filtered after cooling. The yellow solid was recrystallized from aqueous ethanol solution (1:1, v/v) containing 5% conc. HCl to afford 0.25 g (35%) of product 3-hydroxy-4-methyl-2-formylpyridine thiosemicarbazone as the hydrochloride salt: mp 243° C. dec; $^1$H NMR (500 MHz, Me$_2$SO-d$_6$) δ 2.52 (s, 3H, 4-CH$_3$), 3.80 (br, s, 1H, 3-OH, D$_2$O exchangeable), 7.73 (d, 1H, 5H, J$_{5-6}$=4.5 Hz), 8.27 (d, 1H, 6-H, J$_{5-6}$=4.5 Hz), 8.35 (s, 1H, 2-CH), 8.66 and 8.88 (two s, 2H, NH$_2$, D$_2$O exchangeable), 12.07 (s, 1H, NH, D$_2$O exchangeable). HRMS (FAB) m/z cacld. for C$_8$H$_{10}$N$_4$OS 211.0654, found 211.0651. Anal. (C$_8$H$_{10}$N$_4$OS.HCl.H$_2$O) C, H, N.

The hydrochloride was stirred in 10% sodium bicarbonate to yield the free base: mp 227°-228° C. dec (lit. mp 223°-224° C.); $^1$H NMR (500 MHz, Me$_2$SO-d$_6$) δ 2.23 (s, 3H, 4-CH$_3$), 4.80 (br s, 1H, 3-OH, D$_2$O exchangeable), 7.26 (d, 1H, 5H, J$_{5,6}$=5 Hz), 8.05 (d, 1H, 6-H, J$_{5,6}$=5 Hz), 8.20 (s, 2H, NH$_2$, D$_2$O exchangeable), 8.35 (s, 1H, 2-CH), 11.80 (s, 1H, NH, D$_2$O exchangeable).

EXAMPLE XLIV

To a solution of 2-(1,3-dioxolanyl)-4-methyl-3-aminopyridine (0.60 g, 3.3 mmol) in 15 mL of 10% H$_2$SO$_4$ at 0° C. (ice bath) with stirring was added dropwise a solution of NaNO$_2$ (0.38 g, 5.5 mmol) in 3 mL of water. The mixture was stirred at 0° C. for 15 min and then heated in a steam-bath for 30 min. The resulting solution was evaporated at room temperature under reduced pressure to yield 3-hydroxy-4-methyl-2-formylpyridine as a syrup, which was dissolved in 15 mL of water, decolorized with charcoal and filtered. To the filtrate was added a solution of thiosemicarbazide (0.31 g, 3.3 mmol) in 5 mL of 5% HCl. The mixture was refluxed for 30 min, cooled and the yellow precipitate was filtered, washed with water, and recrystallized from aqueous ethanol solution (1:1, v/v) containing 5% conc. HCl to afford 0.21 g (30%) of product: the mp and all spectroscopic data were identical with those obtained in Example XLIII.

EXAMPLE XLV

A mixture of 5-acetoxy-4-methyl-2-acetoxymethylpyridine (6.2 g, 4.5 mmol) and 200 mL of conc. HCl was refluxed for 1 h. After cooling, the reaction mixture was evaporated to dryness under reduced pressure and the residue was purified by silica gel column chromatography (EtOAc-MeOH, 7:3, v/v) to give 3.8 g (97%) of product, 5-hydroxy-4-methyl-2-hydroxymethylpyridine: mp 161°-162° C.: $^1$H NMR (90 MHz, Me$_2$SO-d$_6$) δ 2.33 (s, 3H, 4-CH$_3$), 4.70 (s, 2H, 2-CH$_2$), 7.67 (s, 1H, 3-H), 8.22 (s, 1H, 6-H); HRMS (FAB) m/z cacld. for C$_7$H$_9$NO$_2$ 140.0711, found 140.0736.

EXAMPLE XLVI

Method A. To a solution of 5-hydroxy-4-methyl-2-hydroxymethylpyridine (3.9 g, 28 mmol) in 100 mL of ethanol was added MnO$_2$ (10.0 g, 0.12 mmol) and the reaction mixture was heated to reflux for 2 h with stirring. The mixture was filtered and the filtrate was concentrated under reduced pressure to 80 mL. Because the aldehyde, 5-hydroxy-4-methyl-2-formylpyridine, is unstable, conc. HCl (8 mL) was added immediately. Thiosemicarbazide (1.5 g, 17 mmol) was added to the aldehyde solution with stirring and the reaction mixture was heated to reflux for 30 min. The precipitate was filtered upon cooling and recrystallized in aqueous ethanol solution (1:1, v/v) containing 5% conc. HCl to afford 3.3 g (81%) of product, 5-hydroxy-4-methyl-2-formylpyridine thiosemicarbazone: mp 229° C.; $^1$H NMR (500 MHz, Me$_2$SO-d$_6$) δ 2.33 (s, 3H, 4-CH$_3$), 4.01 (br s, 1H, 5-OH, D$_2$O exchangeable), 8.02 (s, 1H, 3-H), 8.20 (s, 1H, 6-H), 8.22 (s, 1H, 2-CH), 8.58 (s, 2H, NH$_2$, D$_2$O exchangeable), 12.0 (s, 1H, NH, D$_2$O exchangeable). HRMS (FAB) m/z cacld. for C$_8$H$_{10}$N$_4$OS 211.0654, found 211.0671. Anal. (C$_8$H$_{10}$N$_4$OS.HCl.H$_2$O) C, H, N.

The hydrochloride was stirred in 10% sodium bicarbonate to yield the free base: mp 220°-222° C. dec; $^1$H NMR (500 MHz, Me$_2$SO-d$_6$) δ 2.15 (s, 3H, 4-CH$_3$), 7.95 (s, 1H, 3-H), 7.97 (s, 1H, 6-H), 8.01 (s, 1H, 2-CH), 8.04 and 8.18 (two s, 2H, NH$_2$, D$_2$O exchangeable), 10.1 (s, 1H, 5-OH, D$_2$O exchangeable), 12.0 (s, 1H, NH, D$_2$O exchangeable).

Method B. This compound was also prepared from the corresponding 5-amino derivative, 2-(1,3-dioxolanyl)-4-methyl-5-aminopyridine, via the aldehyde, 5-hydroxy-4-methyl-2-formylpyridine, by the same procedure described for the synthesis of 3-hydroxy-4-methy-2-formylpyridine thiosemicarbazone. Yield: 0.32 g (46%); the mp and all spectroscopic data were identical with those obtained in Method A.

EXAMPLE XLVII

A mixture of 2,4-dimethyl-3-nitropyridine (5.0 g, 33 mmol) and selenium dioxide (4.5 g, 42 mmol) in anhydrous 1,4-dioxane (100 mL) was refluxed under an atmosphere of nitrogen for 35 h. The reaction mixture was cooled and filtered to remove the precipitated black selenium. The filtrate was evaporated in vacuo to dryness and the residue was chromatographed on a silica gel (120 g) column (CH$_2$Cl$_2$-EtOAc, 10:1, v/v, R$_f$ 0.65) to afford 1.1 g (20%) of white crystals of 4-methyl-3-nitropyridine-2-carboxaldehyde: mp 101°-102° C.; $^1$H NMR (90 MHz, CDCl$_3$) δ 2.35 (s, 3H, 4-CH$_3$), 7.47 (d, 1H, 5-H, J$_{5,6}$=4.5 Hz), 8.72 (d, 1H, 6-H, J$_{5,6}$=4.5 Hz), 9.95 (s, 1H, 2-CHO). Anal. (C$_7$H$_6$N$_2$O$_3$) C, H, N.

EXAMPLE XLVIII

4-Methyl-5-nitropyridine-2-carboxaldehyde was prepared from the nitro derivative, 5-nitro-2,4-dimethylpyridine, by the same procedure described for the synthesis of Example XLVII, except that the reaction time was 4 h. Yield: 6.0 g (55%); mp 82°-83° C. (lit. 81°-82° C.); TLC, R$_f$0.86 (CH$_2$Cl$_2$/EtOAc, 3:2, v/v); $^1$H NMR (90 MHz, CDCl$_3$) δ 2.70 (s, 3H, 4-CH$_3$), 7.90 (s, 1H, 3-H), 9.20 (s, 1H, 6-H), 10.10 (s, 1H, 2-CHO).

EXAMPLE XLIX

To 0.75 g (14 mmol) of 4-methyl-3-nitropyridine-2-carboxaldehyde in 100 mL of toluene was added 40 mg of p-toluenesulfonic acid monohydrate and 2 mL of ethylene glycol. The reaction mixture was refluxed with stirring, using a Dean-stark trap to remove the water formed during condensation until complete disappearance of the starting material was observed. The mixture was cooled and then washed with 25 mL of 10% NaHCO$_3$ solution, followed by 25 mL of water. The toluene layer was dried over anhydrous MgSO$_4$ and the solvent was removed under reduced pressure.

The residue was chromatographed on a silica gel (120 g) column (CH$_2$Cl$_2$-EtOAc, 10:1, v/v, R0.42) to afford 1.1 g (85%) of white crystals of 2-(1,3-dioxolanyl)-4-methyl-3-nitropyridine: mp 46°–48° C.; $^1$H NMR (90 MHz, CDCl$_3$) δ 2.40 (s, 3H, 4-CH$_3$), 4.07 (s, 4H, CH$_2$CH$_2$), 6.05 (s, 1H, 2-CH), 7.30 (d, 1H, 5-H, J$_{5,6}$=4.5 Hz), 8.60 (d, 1H, 6-H, J$_{5,6}$=4.5 Hz). Anal. (C$_9$H$_{10}$N$_2$O$_4$) C, H, N.

EXAMPLE L 2-(1,3-Dioxolanyl)-4-methyl-5-nitropyridine was synthesized by the method of Example XLIX except that the starting material was 4-methyl-5-nitropyridine-2-carboxaldehyde. Yield: 2.3 g (91%); mp 77°–79° C.; (lit mp 77° C.); TLC, R$_f$ 0.74 (CH$_2$Cl$_2$/EtOAc, 3:2, v/v); $^1$H NMR (90 MHz, CDCl$_3$) δ 2.65 (s, 3H, 4-CH$_3$), 4.10 (s, 4H, CH$_2$CH$_2$), 5.85 (s, 1H, 2-CH), 7.50 (s, 1H, 3-H), 9.12 (s, 1H, 6-H). Anal. (C$_9$H$_{10}$N$_2$O$_4$) C, H, N.

EXAMPLE LI

The nitro derivative, 2-(1,3-dioxolanyl)-4-methyl-3-nitropyridine (1.1 g, 5.2 mmol), was dissolved in 200 mL of ethanol and hydrogenated in a Parr apparatus under 50 psi of pressure in the presence of 10% Pd-C (200 mg) for 20 h. After filtration, the filtrate was evaporated under reduced pressure to give the product (0.9 g, 94%) as a syrup, ninhydrin positive 2-(1,3-dioxolanyl)-4-methyl-3-aminopyridine; $^1$H NMR (90 MHz, CDCl$_3$) δ 2.12 (s, 3H, 4-CH$_3$), 4.05 (m, 4H, CH$_2$CH$_2$), 4.10 (br s, 2H, 3-NH$_2$, D$_2$O exchangeable), 5.76 (s, 1H, 2-CH), 6.92 (d, 1H, 5-H, J$_{5,6}$=4.5 Hz), 7.86 (d, 1H, 6-H, J$_{5,6}$=4.5 Hz). Anal. (C$_9$H$_{12}$N$_2$O$_2$) C, H, N.

EXAMPLE LII 2-(1,3-Dioxolanyl)-4-methyl-5-aminopyridine was synthesized by methodology used for Example LI except that the starting material was 2-(1,3-dioxolanyl)-4-methyl-5-nitropyridine. Yield: 1.2 g (92%); mp 79°–80° C.; $^1$H NMR (90 MHz, CDCl$_3$) δ 2.15 (s, 3H, 4-CH$_3$), 3.70 (br s, 2H, 5-NH$_2$, D$_2$O exchangeable), 4.10 (m, 4H, CH$_2$CH$_2$), 5.70 (s, 1H, 2-CH), 7.15 (s, 1H, 3-H), 8.00 (s, 1H, 6-H). Anal. (C$_9$H$_{12}$N$_2$O$_2$) C, H, N.

The following examples show the usefulness of the compounds of the second aspect of the invention:

EXAMPLES LIII–LVI

This set of experiments contrasts the use of the compounds 3- and 5-hydroxy-2-formylpyridine thiosemicarbazone with the compounds of the invention which are the corresponding 4-methyl-substituted compounds. Examples LIII and LIV are reference examples, while Examples LV and LVI represent compounds of the invention. In each of these examples, DMSO is used for solubilization.

Example LIII

3-Hydroxy-2-formylpyridine thiosemicarbazone was administered to mice bearing the L1210 leukemia by intraperitoneal injection in DMSO solution as the injection form, beginning 24 hours after tumor implantation, with the optimum daily dosage being 40 mg/kg. Administration was once per day for a total of six consecutive days to a representative sample population. At least five mice were tested at each dosage level. The average percentage change in body weight from onset to termination of the therapy was +1.5. A value T/C×100 is calculated, which is the ratio of the survival time of treated to control animals×100, and has a value of 114.

Example LIV

5-Hydroxy-2-formylpyridine thiosemicarbazone was administered to mice bearing the L1210 leukemia by intraperitoneal injection in DMSO solution as the injection form, beginning 24 hours after tumor implantation, with the optimum daily dosage being 40 mg/kg. Administration was once per day for a total of six consecutive days to a representative sample population. At least five mice were tested at each dosage level. The average percentage change in body weight from onset to termination of the therapy was +1.8. A value T/C×100 is calculated, which is the ratio of the survival time of treated to control animals×100, and has a value of 132.

Example LV

3-Hydroxy-4-methyl-2-formylpyridine thiosemicarbazone was administered to mice bearing the L1210 leukemia by intraperitoneal injection in DMSO solution as the injection form, beginning 24 hours after tumor implantation, with the optimum daily dosage being 40 mg/kg. Administration was once per day for a total of six consecutive days to a representative sample population. At least five mice were tested at each dosage level. The average percentage change in body weight from onset to termination of the therapy was +0.5. A value T/C×100 is calculated, which is the ratio of the survival time of treated to control animals×100, and has a value of 135.

Example LVI

5-Hydroxy-4-methyl-2-formylpyridine thiosemicarbazone was administered to mice bearing the L1210 leukemia by intraperitoneal injection in DMSO solution as the injection form, beginning 24 hours after tumor implantation, with the optimum daily dosage being 40 mg/kg. Administration was once per day for a total of six consecutive days to a representative sample population. At least five mice were tested at each dosage level. The average percentage change in body weight from onset to termination of the therapy was −7.4. A value T/C×100 is calculated, which is the ratio of the survival time of treated to control animals×100, and has a value of 138.

EXAMPLES LVII–LIX

Example LVII

5-Hydroxy-2-formylpyridine thiosemicarbazone was administered to mice bearing the L1210 leukemia by intraperitoneal injection in suspension as the injection form, beginning 24 hours after tumor implantation, with the optimum daily dosage being 60 mg/kg. Administration was once per day for a total of six consecutive days to a representative sample population. At least five mice were tested at each dosage level. The average percentage change in body weight from onset to termination of the therapy was +4.6. A value T/C×100 is calculated, which is the ratio of the survival time of treated to control animals×100, and has a value of 146.

Example LVIII

3-Hydroxy-4-methyl-2-formylpyridine thiosemicarbazone was administered to mice bearing the L1210 leukemia by intraperitoneal injection in a suspension as the injection form, beginning 24 hours after tumor implantation, with the optimum daily dosage being 50 mg/kg. Administration was once per day for a total of six consecutive days to a representative sample population. At least five mice were tested at each dosage level. The average percentage change in body weight from onset to termination of the therapy was +0.9. A value T/C×100 is calculated, which is the ratio of the survival time of treated to control animals×100, and has a value of 168.

Example LIX

5-Hydroxy-4-methyl-2-formylpyridine thiosemicarbazone was administered to mice bearing the L1210 leukemia by intraperitoneal injection in a suspension as the injection form, beginning 24 hours after tumor implantation, with the optimum daily dosage being 40 mg/kg. Administration was once per day for a total of six consecutive days to a representative sample population. At least five mice were tested at each dosage level. The average change in body weight from onset to termination of the therapy was −3.4. A value T/C×100 is calculated, which is the ratio of the survival time of treated to control animals×100, and has a value of 186.

What is claimed is:

1. A compound of the formula

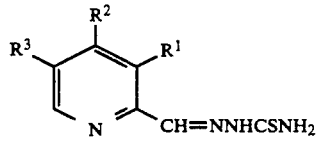

wherein
either (a) $R^1$ is —$NHR^4$ or —$NR^4R^5$ and $R^3$ is hydrogen or (b) $R^3$ is —$NHR^4$, —$NR^4R^5$ or OH and $R^1$ is hydrogen;
$R^2$ is hydrogen or $C_{1-4}$ lower alkyl;
$R^4$ is hydrogen, hydroxyl or $C_{1-4}$ lower alkyl; and
$R^5$ is $C_{1-4}$ lower alkyl;
provided that $R^1$ and $R^2$ cannot both be hydrogen when $R^3$ is $N(CH_3)_2$ or OH;
or a pharmaceutically acceptable salt or hydrate thereof.

2. A compound of claim 1 which is 3-amino-2-formylpyridine thiosemicarbazone or a pharmaceutically acceptable salt or hydrate thereof.

3. A compound of claim 1 which is 5-amino-2-formylpyridine thiosemicarbazone or a pharmaceutically acceptable salt or hydrate thereof.

4. A compound of claim 1 which is 3-amino-4-methyl-2-formylpyridine thiosemicarbazone or a pharmaceutically acceptable salt or hydrate thereof.

5. A compound of claim 1 which is 5-amino-4-methyl-2-formylpyridine thiosemicarbazone or a pharmaceutically acceptable salt or hydrate thereof.

6. A compound of claim 1 which is 5-hydroxyamino-4-methyl-2-formylpyridine thiosemicarbazone or a pharmaceutically acceptable salt or hydrate thereof.

7. The compound 5-hydroxy-4-methyl-2-formylpyridine thiosemicarbazone or a pharmaceutically acceptable salt or hydrate thereof.

* * * * *

UNITED STATES PATENT AND TRADEMARK OFFICE
CERTIFICATE OF CORRECTION

PATENT NO. : 5,281,715
DATED : January 25, 1994
INVENTOR(S) : Alan C. SARTORELLI et al.

It is certified that error appears in the above-indentified patent and that said Letters Patent is hereby corrected as shown below:

On the cover page of the patent, column 1, line 17 of the section "Publications", change "3-Nitropicolines" to --3-Nitropicoline--; and
Line 27, change "9.2-Formyl" to --9. 2-Formyl--.

Column 1, line 21, change "chose" to --chosen--; and
Line 33, change "bazones" to --bazone--.

Column 2, line 28, change "alkyl" to --alkyl,--; and
Line 55, change "40" to --4--.

Column 5, line 42, change "HZ" to --Hz--.

Column 6, line 68, change "$(C_7H_9N_5S.O.4H_2O)$" to --$(C_7H_9N_5S \cdot O \cdot 4H_2O)$--.

Column 7, line 12, change "$(C_8H_{11}N_5S.HCl.H_2O)$" to --$(C_8H_{11}N_5S \cdot HCl \cdot H_2O)$--;
Line 25, change "$(C_8H_{11}N_5S.HCl.H_2O)$" to --$(C_8H_{11}N_5S \cdot HCl \cdot H_2O)$--; and
Line 30, change "(0.36 g, 4 mmol)" to --(0.36 g, 4 mmol)--.

Column 8, line 47, change "11 30" to --11.30--.

Column 9, line 19, change "(i,3-dioxolanyl)" to --(1,3-dioxolanyl)--

UNITED STATES PATENT AND TRADEMARK OFFICE
CERTIFICATE OF CORRECTION

PATENT NO. : 5,281,715
DATED : January 25, 1994
INVENTOR(S) : Alan C. SARTORELLI et al.

It is certified that error appears in the above-indentified patent and that said Letters Patent is hereby corrected as shown below:

Column 10, line 1, change "$C_9H_{13}N_5O_2S_2.0.75$" to --$C_9H_{13}N_5O_2S_2 \cdot 0.75$--;
Line 31, change "s, 1H., NH, $D_2O$" to --s, 1H, NH, $D_2O$--; and
Line 52, change "baring" to --bearing--.

Column 16, line 15, change "($C_8H_{10}N_4OS.HCl.H_2O$)" to --($C_8H_{10}N_4OS \cdot HCl \cdot H_2O$)--.

Column 17, line 2, change "R0.42" to --$R_f$ 0.42--.

Signed and Sealed this

Twenty-eighth Day of November 1995

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,281,715
DATED : January 25, 1994
INVENTOR(S) : Alan Sartorelli, Tai-Shun Lin It is certified that error appears in the above-identified patent and that said Letters Patent is hereby corrected as shown below:

Column 1, line 14, insert the following information:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

*Attest:*

Q. TODD DICKINSON

*Attesting Officer*   *Acting Commissioner of Patents and Trademarks*